United States Patent
Allen et al.

(10) Patent No.: US 12,257,098 B2
(45) Date of Patent: Mar. 25, 2025

(54) SIGNAL TRANSMITTER FOR A RADIOTHERAPY DEVICE

(71) Applicant: Elekta Limited, Crawley (GB)

(72) Inventors: John Allen, West (GB); Adrian Smith, Crawley (GB)

(73) Assignee: Elekta Limited, Crawley (GB)

( * ) Notice: Subject to any disclaimer, the term of this patent is extended or adjusted under 35 U.S.C. 154(b) by 308 days.

(21) Appl. No.: 17/758,610

(22) PCT Filed: Jan. 13, 2021

(86) PCT No.: PCT/EP2021/050551
§ 371 (c)(1),
(2) Date: Jul. 11, 2022

(87) PCT Pub. No.: WO2021/144295
PCT Pub. Date: Jul. 22, 2021

(65) Prior Publication Data
US 2023/0036428 A1 Feb. 2, 2023

(30) Foreign Application Priority Data
Jan. 14, 2020 (GB) .................................. 2000533

(51) Int. Cl.
*A61B 6/00* (2024.01)
*A61N 5/10* (2006.01)
(52) U.S. Cl.
CPC .............. *A61B 6/56* (2013.01); *A61N 5/1048* (2013.01); *A61N 5/1077* (2013.01)

(58) Field of Classification Search
CPC ....... A61B 6/56; A61N 5/1048; A61N 5/1077
See application file for complete search history.

(56) References Cited

U.S. PATENT DOCUMENTS

2006/0079764 A1* 4/2006 Wright .................. A61B 5/704
600/431
2006/0093089 A1* 5/2006 Vertatschitsch ...... A61N 5/1049
378/65

(Continued)

FOREIGN PATENT DOCUMENTS

WO 2016176265 11/2016
WO WO-2019143972 A2 7/2019

OTHER PUBLICATIONS

"International Application Serial No. PCT/EP2021/050551, International Search Report dated Apr. 28, 2021", (Apr. 28, 2021), 3 pgs.

(Continued)

*Primary Examiner* — Blake C Riddick
(74) *Attorney, Agent, or Firm* — Schwegman Lundberg & Woessner, P.A.

(57) ABSTRACT

A wireless signal transmitter is provided for a radiotherapy device, said radiotherapy device being configured to provide radiation to a subject via a source of radiation, and further being configured to output a non-continuous beam of radiation, wherein said non-continuous beam of radiation has a first, time-related property associated therewith. The wireless signal transmitter is configured to wirelessly transmit a signal comprising data regarding the first, time-related property that is associated with the non-continuous beam of radiation, to a wireless signal receiver.

14 Claims, 3 Drawing Sheets

(56) References Cited

U.S. PATENT DOCUMENTS

| | | | |
|---|---|---|---|
| 2008/0009731 A1* | 1/2008 | Maschke | A61N 5/1049 600/1 |
| 2011/0046481 A1* | 2/2011 | Mate | A61N 5/1049 600/427 |
| 2012/0312961 A1* | 12/2012 | Raleigh | A61B 6/542 250/206 |
| 2013/0006036 A1* | 1/2013 | Raleigh | A61N 5/1077 382/128 |
| 2015/0007390 A1 | 1/2015 | Haider et al. | |
| 2018/0185669 A1* | 7/2018 | Kuusela | A61N 5/1031 |
| 2018/0199904 A1 | 7/2018 | Ganguly et al. | |
| 2018/0243584 A1* | 8/2018 | Nord | A61N 5/1081 |
| 2019/0134425 A1* | 5/2019 | van Baar | A61N 5/1077 |
| 2019/0201715 A1* | 7/2019 | Li | A61N 5/1048 |
| 2019/0247676 A1* | 8/2019 | Peltola | A61N 5/103 |
| 2019/0290237 A1 | 9/2019 | Kuwata et al. | |
| 2019/0336795 A1* | 11/2019 | Zhou | A61N 5/1081 |
| 2020/0061390 A1* | 2/2020 | Ma | A61N 5/1048 |
| 2020/0346041 A1* | 11/2020 | Krishnaswamy | A61N 5/1045 |
| 2020/0360727 A1* | 11/2020 | Liu | A61N 5/1045 |
| 2020/0368557 A1* | 11/2020 | Harper | A61N 5/1045 |
| 2021/0030306 A1* | 2/2021 | Leussler | A61N 5/1049 |

OTHER PUBLICATIONS

"International Application Serial No. PCT/EP2021/050551, Written Opinion dated Apr. 28, 2021", (Apr. 28, 2021), 5 pgs.

"United Kingdom Application Serial No. 2000533.6, Examination Report dated Jul. 6, 2020", (Jul. 6, 2020), 6 pgs.

"United Kingdom Application Serial No. 2000533.6, Examination Report dated Oct. 26, 2022", 1 pg.

"European Application No. 21701413.3, Examination Report dated Sep. 30, 2024", (Sep. 30, 2024), 4 pgs.

\* cited by examiner

SIGNAL TRANSMITTER FOR A RADIOTHERAPY DEVICE

PRIORITY APPLICATIONS

This application is a U.S. National Stage Filing under 35 U.S.C. § 371 from International Application No. PCT/EP2021/050551, filed on Jan. 13, 2021, and published as WO2021/144295 on Jul. 22, 2021, which claims the benefit of priority to United Kingdom Application No. 2000533.6, filed on Jan. 14, 2020; the benefit of priority of each of which is hereby claimed herein, and which applications and publication are hereby incorporated herein by reference in their entireties.

BACKGROUND

Radiotherapy can be described as the use of ionising radiation, such as X-rays, to treat a human or animal body. Radiotherapy is commonly used to treat tumours within the body or skin of a patient or subject. In such treatments, ionising radiation is used to irradiate, and thus destroy or damage, cells which form part of the tumour.

A radiotherapy device typically comprises a gantry which supports a beam generation system (or sub-system), or other source of radiation, and which is rotatable around a patient, supported on a support surface such as a table. For example, for a linear accelerator (linac) device, the beam generation sub-system may comprise a source of radio frequency energy, a source of electrons, an accelerating waveguide, a beam shaping apparatus, and so on.

Modern radiotherapy treatment uses techniques to target the tumour (or other target region) as accurately as possible and to reduce the radiation dose to healthy tissue, thereby providing a safer treatment for the patient. For example, a standard approach is to direct the radiation towards the target region from a plurality of different angles, for example by rotating a source of radiation around the patient by use of a rotating gantry. In this case, the angles at which radiation is applied are selected such that each beam of radiation passes through the target region. In this way, a cumulative radiation dose may be built up at the target region over the course of a treatment arc. However, because the radiation is applied from a plurality of different angles, the same, high, cumulative radiation dose is not built up in any portion of the healthy tissue. Therefore, each unit volume of the healthy tissue receives a smaller radiation dose, relative to a unit volume of the target region.

Many radiotherapy devices include, and/or work in conjunction with, one or more so-called 'peripheral' systems, which provide functionality other than the provision of ionising radiation per se. Examples of such 'peripheral' systems include imaging systems that may include a source of imaging radiation and one or more imaging panels that are configured to detect radiation at a particular energy level or levels. For example, known radiotherapy devices may work in conjunction with kV (kiloVolt) and/or MV (MegaVolt) imaging panels. Another example of peripheral systems for a radiotherapy device is quality assurance (QA) devices, which can be used for checking the outputs of a radiotherapy device, to provide QA in relation to the device. In order for such checks to be run, the QA device is usually located remote to the source of the ionising radiation. For example, if the source of ionising radiation is located on a rotating gantry, the QA Device may be located on the patient support surface, which generally does not rotate but may be linearly moveable. Types of QA device that may be used in conjunction with a radiotherapy device include (but are not limited to): an ion chamber (or ion array), a water tank with radiation detector, an MV imaging panel, and one or more arrays of diodes or other electronic radiation detectors.

In order for a peripheral system to work successfully in and/or in conjunction with a radiotherapy device, the peripheral system should be configured so that the accuracy of its outputs is not adversely affected by the inherent operational characteristics of the radiotherapy device. For example, the peripheral system should be configured to accommodate the pulsed nature of the ionising radiation that is typically output by a radiotherapy device.

SUMMARY

In general terms; a device, devices, system and method are provided for wirelessly transmitting signals regarding a radiotherapy device, and/or regarding its operation, to one or more peripheral devices with which the radiotherapy device is configured to operate. The so-called 'peripheral device' may in fact comprise one or more devices, systems or sub-systems. For example, the peripheral device may comprise an imaging device, a diagnostic device or a testing device, or any other suitable device, system or sub-system that can operate in association with, or in conjunction with, a radiotherapy device. For example, the peripheral device may be configured or configurable to check the outputs of a radiotherapy device, or to form an image using the outputs of a radiotherapy device or to detect or diagnose a fault in the operation of a radiotherapy device.

Wireless signalling, for example radiofrequency (RF) signalling, may be used to communicate information regarding the radiotherapy device, or its operation, from a wireless signal transmitter that is associated with the radiotherapy device to a wireless signal receiver that is associated with the peripheral device. The information may involve a time-related property of the operation of the radiotherapy device. For example, the radiotherapy device may be configured to output a non-continuous (i.e. pulsed or intermittent) beam of radiation, and the time-related property may relate to, for example, the timing, frequency or duration of the instances (or pulses) of that output radiation. The information may be used to synchronise the operation of the peripheral with the pulsed output of the radiotherapy device, or to enable the peripheral to operate in a manner that accommodates the pulsed output of the radiotherapy device, and does not cause it to mistake the pulsed output as being indicative of incorrect or non-continuous operation of the radiotherapy device.

The wireless signalling may be conducted using relatively low security signals, since a radiotherapy environment is generally sealed, or closed off, from the outside world and its atmosphere is relatively empty of wireless signals. The wireless signalling may be conducted using a relatively short range protocol since typically the distances between the radiation source of a radiotherapy device and any peripherals with which it operates is not large. The wireless signalling may be conducted using signals that have relatively low latency and low jitter, to accommodate, for example, the very high frequency at which output radiation from a radiotherapy device is typically pulsed.

According to an aspect; a wireless signal transmitter for a radiotherapy device is provided, said radiotherapy device being configured to provide radiation to a subject via a source of radiation. Said source of radiation is configured to output a non-continuous beam of radiation, wherein said non-continuous beam of radiation has a first, time-related property associated therewith. The wireless signal transmitter is configured to wirelessly transmit a signal comprising data regarding the first, time-related property that is associated with the non-continuous beam of radiation, to a wireless signal receiver.

The radiation provided by the radiotherapy device may be therapeutic radiation. The subject may be a human or animal patient.

The non-continuous beam of radiation may be an intermittent or 'pulsed' beam of radiation. For example, it may be pulsed at high frequency, for example at between 6 and 400 pulses per second (pps). The lower pps frequencies will result in lower dose-rates so may not be used as often in clinical use. However they may be used when the dose-rate is automatically modulated and these lower dose-rate may need to be checked by a QA device. The frequency of the pulsed beam of radiation that is output from the radiotherapy device may be substantially similar to the frequency of a pulsed RF wave that is input into a waveguide or into another aspect/part of the radiotherapy device. Transmission of the first, time-related property may enable a device, at the receiving end, to synchronise or coordinate its operation and/or its measurements with the non-continuous beam of radiation that the radiotherapy device is configured to output.

The first, time-related property associated with the non-continuous beam of radiation may comprise any of: a frequency of the pulsing; a time at which a pulse occurs or occurred or will occur; a time period after which a subsequent pulse can be expected to occur; a duration of a pulse; or any other suitable time-related property. The time-related property may relate to the non-continuous beam as a whole, and/or it may relate to one or more individual pulses.

The wireless signal transmitter may be located in or on the radiotherapy device. The wireless signal transmitter may be removably connected to the radiotherapy device. The wireless signal receiver may be comprised within a radiation beam generation sub-system of the radiotherapy device. The wireless signal receiver may connect to, or communicate with, a controller that is configured to control (a part of) the radiation beam generation sub-system.

The radiotherapy device may be, for example, a linear accelerator (linac) device.

The radiotherapy device may be configured to operate in conjunction with a peripheral device, and the wireless signal transmitter may be configured to wirelessly transmit the signal to a wireless signal receiver that is associated with said peripheral device. For example, the wireless signal receiver may be located in or on the peripheral device. For example, the wireless signal receiver may be removably connected to the peripheral device.

The wireless signal transmitter may be configured to transmit radiofrequency (RF) signals. The wireless signal transmitter may be configured to transmit optical signals, such as InfraRed (IR) signals. The wireless signal transmitter may be configured to transmit signals via WiFi or Bluetooth™ or via any suitable proprietary or custom low latency and/or low jitter standard.

As will be known to the skilled reader; an RF signal itself typically is not secure, in the sense that any suitable radio receiving equipment can usually detect its presence. However, it is possible for an RF signal to comprises some 'metadata', which can be sent in either unencrypted or encrypted form. When metadata is sent in an encrypted form, via RF signalling, then pairing, bonding or some other secure technique might be necessary in order for the peripheral device (or a controller associated with its wireless signal receiver) to 'read' this data.

The wireless signal transmitter may be configured to transmit non-encrypted wireless signals, or wireless signals that do not comprise encrypted data or metadata. That is; the wireless signal transmitter may be configured to transmit signals via an open published protocol. In some arrangements, the wireless signal transmitter may be configured to transmit signals via a private closed protocol.

The wireless signal transmitter may be configured to transmit signals in a relatively low-security manner. For example, it may not require 'pairing', or 'bonding', or another authentication process to occur, before a wireless signal receiver is permitted to receive its wireless signals. For example, the wireless signal transmitter may be configured to operate in a 'broadcast' mode, in which it does not seek a specific receiver identity or address, for receiving its wireless signals.

The wireless signal transmitter may be configured to transmit a signal via any suitable frequency or frequencies. For example, it may use an Industrial, Scientific, Medical (ISM) frequency. It may transmit via an open frequency or via a secret or closed frequency.

The radiotherapy device may comprise a rotatable member and the wireless signal transmitter may be provided in or on said rotatable member. For example, the rotatable member may be a gantry or a slip ring. For example, the wireless signal transmitter may be comprised in, within, on or in connection to a radiation source that is provided on a rotatable member of the radiotherapy device.

The radiotherapy device may be configured to operate in conjunction with a peripheral device, wherein said peripheral device is configured not to rotate with the rotatable member of the radiotherapy device, and wherein the wireless signal transmitter is configured to wirelessly transmit the signal to a wireless signal receiver that is associated with said peripheral device. For example, the wireless signal receiver may be comprised in, within, on or in connection to a peripheral device that is configured to be placed on a non-rotatable patient support surface or on another stationary surface or location, when in use in conjunction with the radiotherapy device.

The wireless signal transmitter may be configured to wirelessly transmit a signal comprising data regarding a second property, which is associated with the non-continuous beam of radiation or with another aspect of the radiotherapy device, to a wireless signal receiver. For example, the second property may not be a time-related property associated with the non-continuous beam of radiation. For example, the second property may comprise meta-data regarding the identity, operation, configuration or constitution of the radiotherapy device. The wireless signal transmitter may be configured to transmit meta-data in addition to transmitting data regarding a first, time-related property associated with the non-continuous beam of radiation.

According to an aspect, a system is provided comprising a radiotherapy device and a wireless signal transmitter, said radiotherapy device being configured to provide radiation to a subject via a source of radiation. Said source of radiation is configured to output a non-continuous beam of radiation, wherein said non-continuous beam of radiation has a first, time-related property associated therewith. The wireless signal transmitter is configured to wirelessly transmit a signal comprising data regarding the first, time-related property that is associated with the non-continuous beam of radiation, to a wireless signal receiver.

According to an aspect, a wireless signal receiver for a peripheral device is provided, wherein said peripheral device is configured to work in conjunction with a radiotherapy device, said radiotherapy device being configured to provide radiation to a subject via a source of radiation. Said source of radiation is configured to output a non-continuous beam of radiation, wherein said non-continuous beam of radiation has a first, time-related property associated therewith. The wireless signal receiver is configured to wirelessly receive a signal comprising data regarding the first, time-related property that is associated with the non-continuous beam of radiation, from a wireless signal transmitter.

The wireless signal receiver may be provided in, on, within or in connection with the peripheral device. For example, it may be removably connectable from and to the peripheral device. It may be configured for use with two or more respectively different peripheral devices.

According to an aspect, a system is provided comprising a peripheral device configured to work in conjunction with a radiotherapy device, and a wireless signal receiver, wherein said radiotherapy device being configured to provide radiation to a subject via a source of radiation. Said source of radiation is configured to output a non-continuous beam of radiation, wherein said non-continuous beam of radiation has a first, time-related property associated therewith. The wireless signal receiver is configured to wirelessly receive a signal comprising data regarding the first, time-related property that is associated with the non-continuous beam of radiation, from a wireless signal transmitter.

According to an aspect, a controller for a wireless signal transmitter is provided, the wireless signal transmitter being configured for use with a radiotherapy device. The controller is configured to cause the wireless signal transmitter to wirelessly transmit a signal to a wireless signal receiver that is associated with a peripheral device with which radiotherapy device is configured to operate, wherein the signal comprises data regarding an aspect of the radiotherapy device.

According to an aspect, a controller for a wireless signal transmitter is provided, the wireless signal transmitter being configured for use with a radiotherapy device, said radiotherapy device being configured to provide radiation to a subject via a source of radiation. Said source of radiation is configured to output a non-continuous beam of radiation, wherein said non-continuous beam of radiation has a first, time-related property associated therewith. The controller is configured to cause the wireless signal transmitter to wirelessly transmit a signal comprising data regarding the first, time-related property that is associated with the non-continuous beam of radiation, to a wireless signal receiver.

According to an aspect, there is provided a method of providing a communicative connection between a radiotherapy device and a peripheral device that the radiotherapy device is configured to operate in association with. The method comprises providing a wireless signal transmitter that is associated with the radiotherapy device and providing a wireless signal receiver that is associated with the peripheral device. The method further comprises configuring the wireless signal transmitter and wireless signal receiver to respectively wirelessly transmit and receive a signal comprising data regarding an aspect of the radiotherapy device.

According to the above method, the radiotherapy device may be configured to provide radiation to a subject via a source of radiation, said source of radiation being configured to output a non-continuous beam of radiation, wherein said non-continuous beam of radiation has a first, time-related property associated therewith. The method may comprise causing the wireless signal transmitter to wirelessly transmit a signal comprising data regarding the first, time-related property that is associated with the non-continuous beam of radiation, to the wireless signal receiver that is associated with the peripheral device.

Any suitable combination of the above aspects may be provided. Except where clearly mutually exclusive, a feature or combination of features or parameter(s) described in relation to any one of the above aspects or described herebelow in relation to a particular arrangement, may be applied to any other aspect or arrangement.

FIGURES

Specific arrangements are described herein, by way of example only, with reference to the figures, of which:

DETAILED DESCRIPTION

Figure 1:
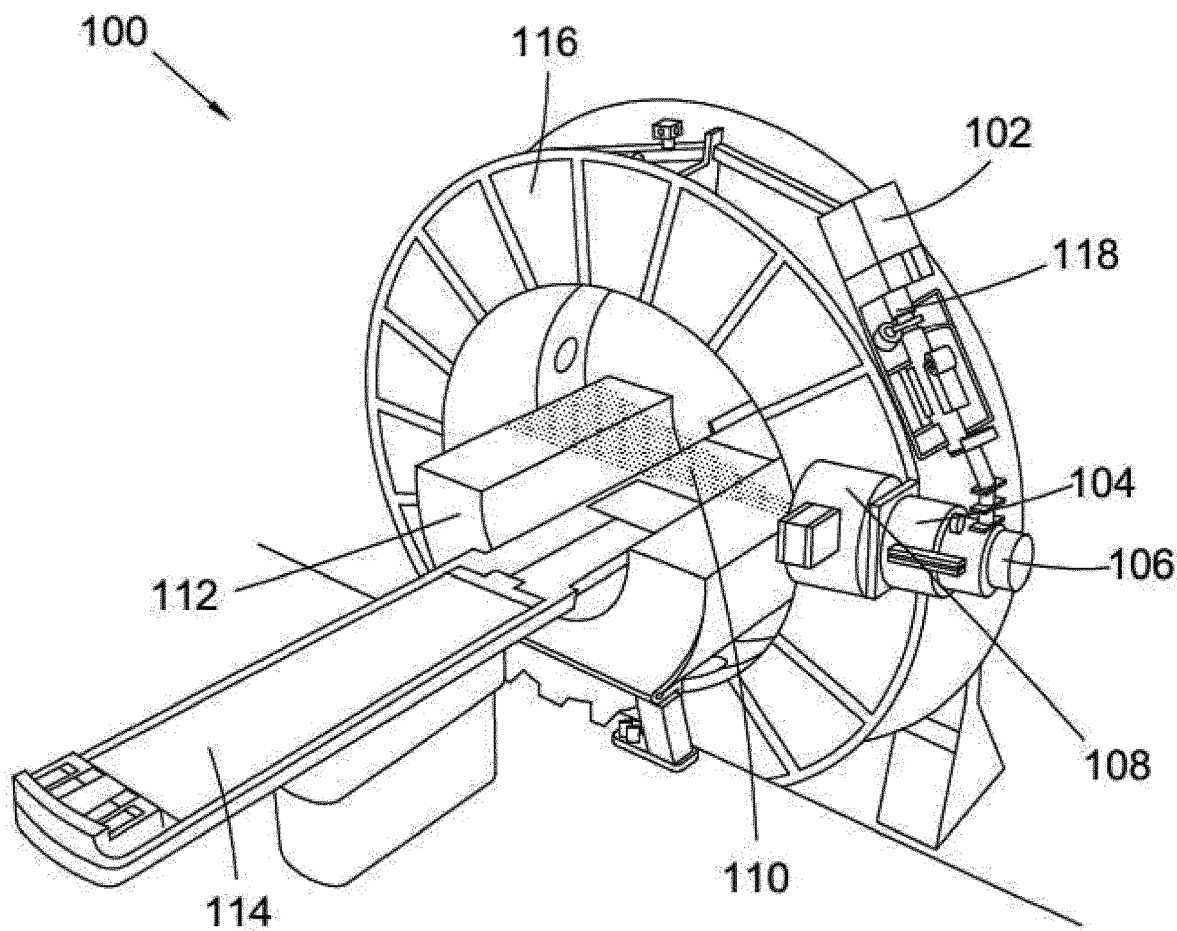
FIG. 1 depicts a radiotherapy device.

FIG. 1 depicts a radiotherapy device suitable for delivering, and configured to deliver, a beam of radiation to a patient during radiotherapy treatment. The device and its constituent components will be described generally for the purpose of providing useful accompanying information for the present arrangements. The device depicted in FIG. 1 is in accordance with the present disclosure and is suitable for use with the disclosed systems and apparatuses. The device in FIG. 1 is an MR-linac, which is a magnetic resonance imaging (MRI) guided radiotherapy system. However the present disclosure is not limited to MR-linacs—it can be applied to any radiotherapy device, for example, but not limited to, a linac (linear accelerator) device.

The device 100 depicted in FIG. 1 is an MR-linac. The device 100 comprises both MR (magnetic resonance) imaging apparatus 112 and radiotherapy (RT) apparatus, comprising a linac device. The MR imaging apparatus 112 is shown in cross-section in FIG. 1. In operation, the MR scanner produces MR images of the patient, and the linac device produces and shapes a beam of radiation and directs it toward a target region within a patient's body in accordance with a radiotherapy treatment plan.

The MR-linac device depicted in FIG. 1 comprises a source of radiofrequency waves 102, a waveguide 104, a source of electrons 106, a radiation source (discussed further below), a collimator 108 such as a multi-leaf collimator configured to collimate and shape the beam, MR imaging apparatus 112, and a patient support surface 114. In use, the device would also comprise a housing (not shown) which, together with the ring-shaped gantry 116, defines a bore. The moveable support surface 114 can be used to move a patient, or other subject or object, into the bore when an MR scan and/or when radiotherapy is to commence, or for testing purposes. The MR imaging apparatus 112, RT apparatus, and a subject support surface actuator are communicatively coupled to a controller or processor. The controller is also communicatively coupled to a memory device comprising computer-executable instructions which may be executed by the controller.

The 'RT apparatus' aspect of the MR-linac of FIG. 1 generally comprises the source of radiation (discussed further below) and a radiation detector (not shown). Typically, the radiation detector is positioned diametrically opposed to the source of radiation. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source in FIG. 1 comprises a 'beam generation sub-system'. It includes the source of radiofrequency waves 102, a source of electrons comprising, in this arrangement, an electron gun 106, and a waveguide 104. The radiation source is attached to the rotatable gantry 116 so as to rotate with the gantry 116. In this way, the radiation source is rotatable around the patient so that the treatment beam 110 can be applied from different angles around the gantry 116. In this arrangement, the gantry is continuously rotatable. In other words, the gantry can be rotated by 360 degrees around the patient, and in fact can continue to be rotated past 360 degrees. But other gantry types are possible. The gantry may be ring-shaped. In other words, the gantry may be a ring-gantry.

The source 102 of radiofrequency waves in this arrangement comprises a magnetron, though other types of radiofrequency wave sources may instead be used. The magnetron 102 in this arrangement is configured to produce radiofrequency waves. It is coupled to the waveguide 104 via a circulator 118, and is configured to pulse radiofrequency waves into the waveguide 104. Radiofrequency waves may pass from the magnetron 102 through an RF input window and into an RF input connecting pipe or tube. The electron gun 106 is also coupled to the waveguide 104 and is configured to inject electrons into the waveguide 104. In the electron gun 106, electrons are thermionically emitted from a cathode filament as the filament is heated. The temperature of the filament controls the number of electrons injected. The injection of electrons into the waveguide 104 is synchronised with the pulsing (or 'pumping') of the radiofrequency waves into the waveguide 104. The design and operation of the magnetron 102, electron gun 106 and waveguide 104 is such that the radiofrequency waves accelerate the electrons to very high energies as the electrons propagate through the waveguide 104.

The design of the waveguide 104 depends on whether the linac accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104. As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets.

The electrons travel toward a heavy metal target which may comprise, for example, tungsten. Whilst the electrons travel through the flight tube, an arrangement of focusing magnets act to direct and focus the beam on the target.

The radiation source is configured to direct a beam 110 of therapeutic radiation toward a patient positioned on the patient support surface 114. When the electrons exiting the waveguide 104 strike the target, X-rays are produced in a variety of directions. A primary collimator may block X-rays travelling in certain directions and may allow only forward travelling X-rays to contribute to the treatment beam 110.

The X-rays may be filtered and may pass through one or more ion chambers for dose measuring. The beam can be shaped in various ways by beam-shaping apparatus, for example by using a multi-leaf collimator 108, before it passes into the patient as part of radiotherapy treatment.

In some implementations, the source of radiation is configured to emit either an X-ray beam or an electron particle beam. Such implementations allow the device to provide electron beam therapy, i.e. a type of external beam therapy where electrons, rather than X-rays, are directed toward the target region. It is possible, in some radiotherapy devices, to 'swap' between a first mode in which X-rays are emitted and a second mode in which electrons are emitted. In essence, it is possible to swap between the first and second modes by moving the heavy metal target in or out of the electron beam path and replacing it (for the second mode) with a so-called 'electron window'. The electron window is substantially transparent to electrons and allows electrons to exit the flight tube.

The subject or patient support surface 114 is generally configured to move linearly, and is configured to move between a first position substantially outside the bore, and a second position substantially inside the bore. In the first position, a patient or subject can mount the patient support surface. The support surface 114, and patient, can then be moved inside the bore, to the second position, in order for the patient to be imaged by the MR imaging apparatus 112 and/or imaged or treated using the RT apparatus. The patient support surface 114 may also be moveable in a substantially vertical plane, for example to accommodate patients of different sizes and physical capabilities, mounting the patient support surface.

The movement of the patient support surface 114 is effected and controlled by a subject support surface actuator, which may be described as an actuation mechanism. The actuation mechanism is configured to move the subject support surface in a direction parallel to, and defined by, the central axis of the bore. The terms 'subject' and 'patient' are used interchangeably herein such that the subject support surface can also be described as a patient support surface. The subject support surface may also be referred to as a moveable or adjustable couch or table.

The MR-linac device depicted in FIG. 1 also comprises MR imaging apparatus 112, however the detailed arrangements described herebelow also apply to radiotherapy devices that have no imaging apparatus, or that have different types of imaging apparatus. The MR imaging apparatus 112 in FIG. 1 is configured to obtain images of a subject positioned, i.e. located, on the subject support surface 114. The MR imaging apparatus 112 may also be referred to as the MR imager. The MR imaging apparatus 112 may be a conventional MR imaging apparatus operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by a controller.

The controller for the MR-linac device of FIG. 1 is a computer, processor, or other processing apparatus. The controller may be a single entity or it may be formed by several discrete processors, which may be physically and/or computationally distinct from one another. For example, the controller may comprise: an MR imaging apparatus processor, which controls the MR imaging apparatus 110; an RT apparatus processor, which controls the operation of the RT apparatus; and a subject support surface processor which controls the operation and actuation of the subject support surface. The controller is communicatively coupled to a memory, e.g. a computer readable medium.

The MR-linac device of FIG. 1 also comprises several other components and systems as will be understood by the skilled person. For example, in order to ensure the linac does not leak radiation, appropriate shielding is also provided.

Many radiotherapy devices, including linear accelerators (linacs) such as the MR-linac of FIG. 1, use pulsed high-power RF (radio frequency) sources (such as the magnetron 102) that generate the power to produce short, widely-space pulses. This type of RF power source results in the radiation output—for example, the beam 110 in FIG. 1—also being pulsed, with approximately the same duty cycle as the RF source. For delivery of treatment, the pulsed (i.e. non-continuous or intermittent) nature of the radiation can normally be accommodated via the design features of the radiotherapy device's radiation dose-monitoring system. Because such a dose-monitoring system is usually designed and supplied by the radiotherapy device manufacture, designing the dose-monitoring system to accommodate the pulsed nature of the output radiation is normally not problematic. However, there are other systems and/or devices that may be affected by the pulsed nature of the radiation. For example, systems or devices that are not (or that may not be) designed and/or made by the same manufacturer as that which makes the radiation-producing components of a radiotherapy device may be susceptible to problems or difficulties with accommodating the pulsed nature of the output radiation. For example, so-called 'peripheral' systems, sub-systems or devices that may be optional add-ons for a radiotherapy device or that may be used in conjunction with a radiotherapy device, for example for testing or QA purposes, may be susceptible to problems or difficulties with accommodating the pulsed nature of the output radiation.

For example, an MV imaging system may detect pulse artefacts on its images, due to the pulsed nature of the output radiation from a therapeutic radiotherapy device. As the skilled reader will be aware; MV imaging equipment may be comprised within/on/in a radiotherapy device, or may be provided separate thereto, for example on the patient support surface or on another support structure. In some arrangements, an MV imager is provided mounted on the rotating gantry of a radiotherapy device. An MV imager generally uses the 'therapeutic' output radiation beam of a radiotherapy device, for imaging. Because, therefore, it is capable of measuring the therapeutic beam, an MV imager can be a useful QA device. However its measurements may be compromised if it does not accommodate the pulsed nature of the therapeutic beam.

For example, peripheral devices such as QA devices that are used to detect and/or to test the outputs of a radiotherapy device may record a noisy signal if their sampling is not suitably designed to accommodate the pulsed (i.e. non-continuous or intermittent) nature of its output radiation. By way of non-limiting example, the therapeutic radiation beam output from a radiotherapy device may be pulsed at a rate of, say, 200 times per second. A QA device that comprises a scanner or detector may also operate in a 'pulsed' manner, for example scanning or detecting at a rate of, say, 20 times per second. If the pulsing of the QA device is not suitably synchronised with the pulsing of the radiation output from the radiotherapy device, this could lead to the QA device detecting (in this particular numerical example) 10 radiation pulses in a first scan and 11 radiation pulses in a second, subsequent scan. Therefore the radiation output from the radiotherapy device would appear 'jagged' to the QA device, even though it is not.

Figure 3:
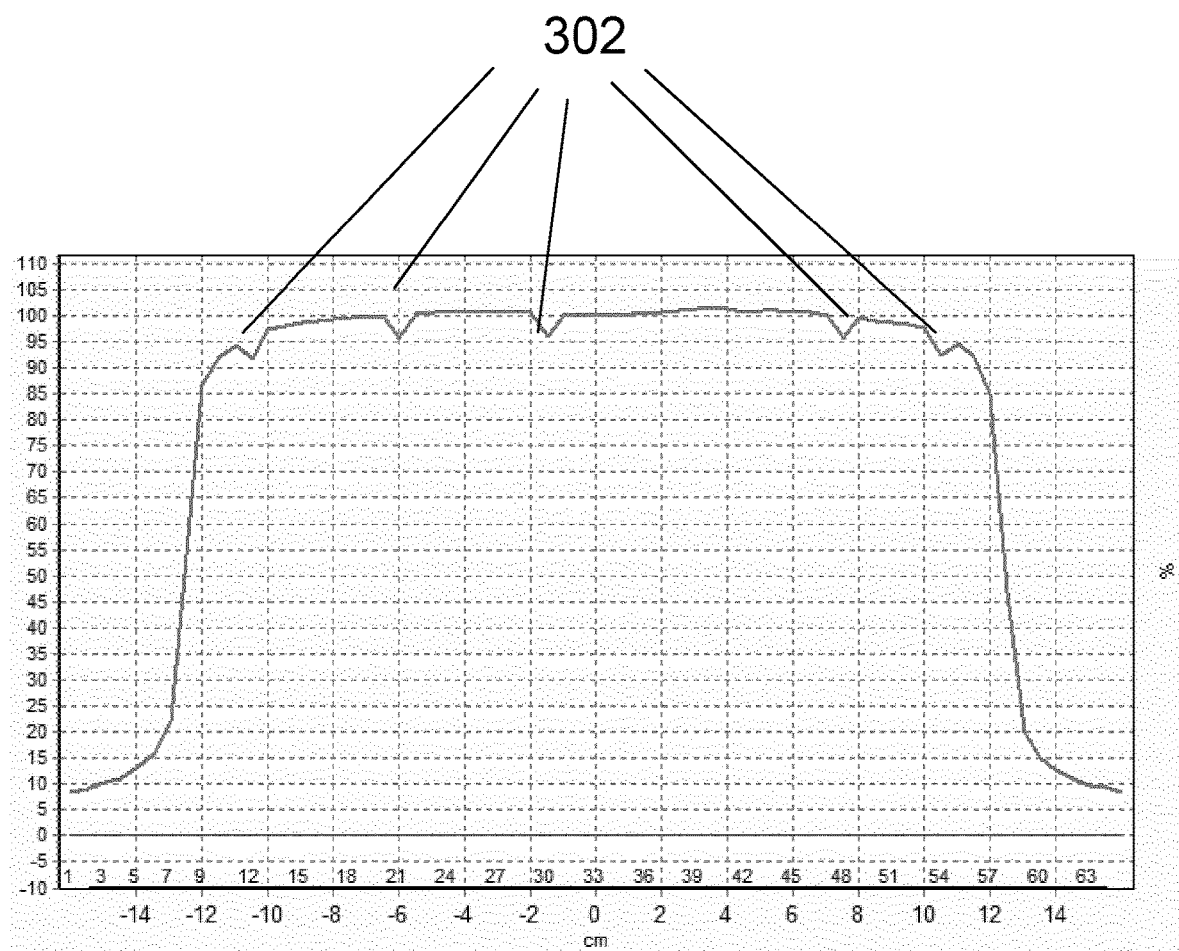
FIG. 3 depicts a profile of radiation measurements taken by an ion chamber that is not synchronised with the linac that is outputting the radiation.

FIG. 3 comprises an example graphical profile 300 of output radiation for a linac, as measured using an ion-chamber array that was not synchronised with the linac. As can be seen, the profile 300 includes measurement artefacts which appear as triangular 'dips' or decreases 302 in the profile 300. These dips 302 do not represent 'real' variations in the radiation output from the linac. Instead, the dips 302 have arisen due to the fact that the ion chamber is read by electronics which sample data a number of times a second. Because the sampling frequency for the electronic samples were not, in this example, synchronised with the pulsed radiation being output from the linac, some measurements had less dose than others. If the profile was viewed in real-time, the triangular dips 302 would appear to move randomly, to any position in the plot.

In order to address possible problems that peripheral systems, sub-systems or devices may encounter when working as part of, or in conjunction with, a radiotherapy device that has a pulsed radiation output, it is known to provide dedicated 'trigger' signals from the sub-system that triggers the radiofrequency (RF) source, within the radiotherapy device. The sub-system that triggers the radiofrequency source is usually part of the beam generation sub-system, such as the magnetron 102 shown in FIG. 1. The 'trigger' signals, which indicate the timing and/or frequency of the RF waves that are pulsed into the waveguide, for generation of the output radiation, are usually transmitted, in known arrangements, via a coaxial cable or other electrical connection. Although this type of connection can enable synchronisation of a peripheral device with the output radiation from the radiotherapy device, in practice its usefulness and the extent to which it can be successfully implemented are limited.

For example, in order to provide an electrical connector for synchronising the output radiation from the radiotherapy device with one or more peripheral devices, the nature and configuration of the electrical connector has to be thought about in advance—usually during design and/or manufacture of the radiotherapy device—and there are often practical difficulties in routing the cable. It is also generally very difficult, if not impossible, to retrofit such a connector to a pre-existing radiotherapy device.

For example, the beam generation sub-system of a radiotherapy device may be mounted on a rotating gantry. Increasingly, radiotherapy devices such as linacs are being designed around relatively compact gantries, some of which utilise slip-rings that power most of the beam generation sub-system on the gantry itself. Conversely, peripheral devices such as QA devices and/or imaging devices often are independent, not incorporated into the radiotherapy device at all, or at least not incorporated into the rotating gantry or slip-ring. Instead, such devices are often mounted on the patient support surface, or on or in another part of the static (non-rotating) 'stand' of the radiotherapy device, for use. This gives rise to the issue of how to safely and reliably route an electrical signal from the rotating gantry or slip-ring, back to the patient table or static stand, without the cables becoming tangled and/or without the need to provide very long lengths of cable, that can be repeatedly wound around a suitable cable reel.

Furthermore, any direct electrical connection has to be thought about with respect to electrical safety, and EMC (electromagnetic compatibility) considerations (e.g. ESD (electrostatic discharge) testing). As the skilled reader will know; EMC considerations generally encompass the consideration of all possible means by which electrical equipment might be affected by other electrical equipment (commonly called interference) or by the electrical environment in which the equipment is used. ESD refers to a specific type of EMC immunity testing. ESD is the sudden flow of electricity that can occur when two objects touch. Often one of the objects is a human, and ESD often occurs when a human touches an electrical connection. Unless they are correctly protected; modern electronics can be harmed by ESD. As a result, in many jurisdictions there are stringent regulatory requirements on electrical connections, especially when they are close to where a patient might be treated. For example, such regulations would usually determine that it is generally not acceptable for the patient to come into contact with an electrical cable. With a direct electrical connection there is also the risk of unintended consequences, should the peripheral system behave in an abnormal way. It will be appreciated that, given the highly sensitive and patient-critical nature of a radiotherapy device, such a risk may be deemed unacceptable.

It has been recognised herein that it is possible to provide coordination, for example synchronisation, between the beam-generation aspects of a radiotherapy device and one or more peripheral systems, sub-systems or devices in a safe, simple, accurate and reliable manner. As a result, the one or more peripheral systems, sub-systems or devices can operate in a manner that accommodates the inherent pulsed (i.e. non-continuous or intermittent) nature of the radiation output from the radiotherapy device, and that can avoid detecting or showing errors, changes or artefacts in relation to the operation of the radiotherapy device at times when it is in fact operating correctly.

In general terms; a wireless signal transmitter is provided, which is configured to wirelessly transmit a signal that enables the coordination of the operation of a radiotherapy device with the operation of one or more peripheral systems, sub-systems or devices. The coordination can involve an aspect of so-called 'synchronisation', wherein the wireless signal transmitter provides signals comprising information regarding the timing and/or the frequency of the radio frequency (RF) waves that are pulsed into the waveguide, in the beam generation sub-system of the radiotherapy device. As the skilled reader will appreciate; the RF waves that are pulsed into the waveguide (largely) determine the frequency of the output radiation, since the latter follows from the former. Put another way; the into RF waves may be regarded as being the 'cause' and the output radiation may be regarded as being the 'effect'.

The signals comprising information regarding the timing and/or the frequency of the radio frequency (RF) waves that are pulsed into the waveguide may be referred to as 'trigger signals'. The trigger signals may not necessarily cause the one or more peripheral systems, sub-systems or devices to 'synchronise' its/their operation, in the sense of operating exactly in time with the operation(s) of the radiotherapy device. However the trigger signals can enable the one or more peripheral systems, sub-systems or devices to 'synchronise' its/their operation in the sense of enabling it/them to 'know' that the output radiation from the radiotherapy device will be pulsed, and to know the timing and/or frequency of those pulses, at least to a highly accurate level of approximation, and to thereby take account of and accommodate the radiation pulses, during operation.

The wireless signal transmitter does not require a wired electrical connection between the radiotherapy device and the one or more peripheral systems, sub-systems or devices, in order to operate successfully. It also does not require a wired electrical connection between a rotating part and a non-rotating or static part of the radiotherapy device. This, at least in some cases, enables the wireless signal transmitter to be retrofitted to an existing radiotherapy device, to improve its operation in conjunction with peripheral systems, sub-systems or devices. It also means that, if inclusion of the wireless signal transmitter is contemplated during design and/or manufacture, the complexity of the considerations involved in implementing it is much reduced, as compared to previously-known systems in which a wired connection would have been required.

Figure 2:
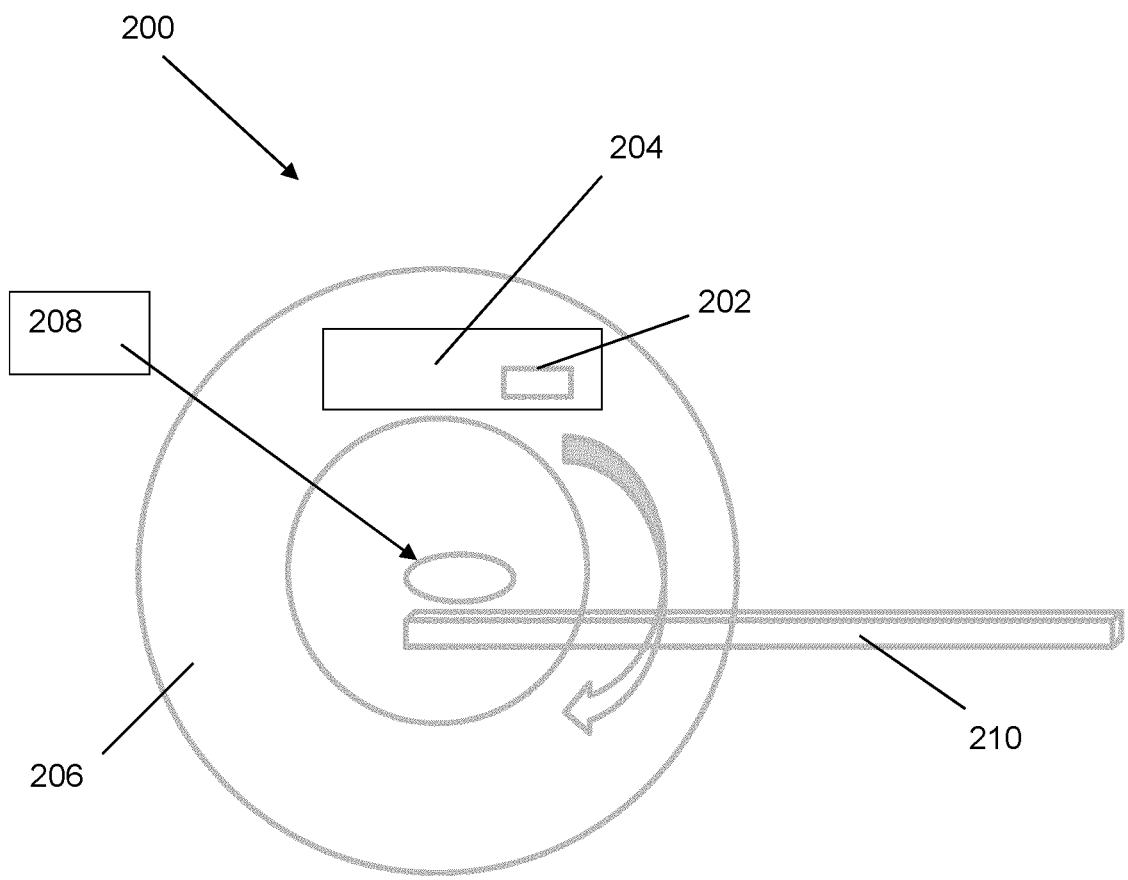
FIG. 2 depicts a radiotherapy device including a wireless transmitter.

FIG. 2 is a simplified schematic diagram, showing an example of a radiotherapy device (in this case, a linac device 200) comprising a wireless signal transmitter 202. The wireless signal transmitter 202 in this example comprises a radiofrequency (RF) pulse signal transmitter, which may be an RF pulse signal transmitter. However other wireless signal transmitter types may instead be used, as discussed further below.

The RF signal transmitter 202 in FIG. 2 is comprised within a beam generation sub-system 204 of the linac 200. The elements and operation of a beam generation sub-system (such as an RF source, an electron source, a waveguide, and so on) have been described hereabove in detail in relation to FIG. 1, and so for brevity will not be repeated in relation to FIG. 2. The beam generation sub-system 204 in this example is provided on a rotating gantry 206. FIG. 2 also shows a peripheral device such as a QA device 208, located on a non-rotating patient support surface 210. The QA device may comprise, for example, an MV imager, an ion chamber array or a diode array. It will be appreciated that the QA device 208 may be removable from the linac 200, but is shown in situ in FIG. 2 for the purpose of the present description. It may be possible to locate the peripheral device elsewhere, on or in another support surface or at any suitable location within the radiotherapy environment.

Although a QA device 208 is shown by way of example in FIG. 2, any other suitable peripheral may be used in place of the QA device 208 in FIG. 2. For example, the peripheral may comprise one or more instruments that are sensitive to the radiation pulse where there performance may be improved by blanking there signals during radiation (anti-synchronisation). For example, the peripheral may comprise any of: a camera; a microphone; or a fibreoptic cable.

The beam generation sub-system 204 incudes a primary pulse generation system (or 'pulse generator'), which is not specifically depicted in FIG. 2, The pulse generator is configured to produce a pulsed RF wave, which is fed into a waveguide to mix with injected electrons, for creation of the pulsed output radiation, as detailed above in relation to FIG. 1. In the example of FIG. 2, the pulse generator is also connected to the RF signal transmitter 202. This connection enables information regarding a timing fiducial, for example the timing and/or the frequency of the pulses generated by the pulse generator, to be conveyed to the RF signal transmitter 202. In turn, the RF signal transmitter 202 can be configured to transmit that timing information to an RF signal receiver located in, on or in connection with, one or more peripheral devices.

The RF signal transmitter 202 can be relatively simple, in terms of both design and operation. In this example, the RF signal transmitter 202 is configured to transmit signals via any suitable, allowed ISM (Industrial, Scientific and Medical) frequency such as, but not limited to, 433 MHz. As the skilled reader will appreciate, there is a wide range of such frequencies that is available for use. It has been recognised herein that, because of the particular and quite unique physical circumstances in which a radiotherapy device is used, the RF signal transmitter can be configured to operate in an open 'broadcast' mode, with little or no security surrounding the signal. For example, the signal may not need to be encrypted and/or there may be no requirement for an authentication process, in order for a receiver to receive the signal. That is; it has been recognised herein that a radiotherapy device (when used correctly) will be located within a sealed 'room', or other environment, the walls or barriers of which are effectively impermeable to most radiation. This is to ensure that the therapeutic radiation output from the radiotherapy device—which is damaging to healthy human tissue and can affect the operation of electronic devices and so on—does not escape from the immediate vicinity of the radiotherapy device. As a result—and in contrast to most modern-day environments—the airwaves in the room within which the radiotherapy device is located, will be largely free of RF and other wireless signals. The risk of the signals that are emitted by the RF signal transmitter 202 being obscured by, or confused with, other RF signals in a radiotherapy environment is therefore very low.

Although not specifically shown in FIG. 2, the QA device 208 therein includes a wireless signal receiver, which in this example comprises an RF signal receiver. The RF signal receiver of the QA device 208 can be configured to wirelessly receive RF signals from the RF signal transmitter 202 that is located on (or in) the linac 200. The RF signal receiver may be tuneable, in order to receive signals via a particular frequency at which the RF signal transmitter 202 is configured (at any given time) to transmit its signals. The RF signal receiver can be configured to receive signals from the RF signal transmitter 202 that include a timing fiducial for the radiotherapy device, and to transmit the timing fiducial to a controller that may be comprised in an entity that also comprise the RF signal receiver, or which may be within the QA device 208. The QA device 208 (or its controller) may then use the timing fiducial in order to synchronise its operation with that of the radiotherapy device, or to otherwise control its operation in order to accommodate the pulsed nature of the radiation that is output by the radiotherapy device.

The RF signal transmitter 202 and RF signal receiver may be configured to undergo a so-called 'handshake' procedure, whereby the RF signal transmitter 202 has to identify itself to the RF signal receiver (and/or vice versa), for authentication purposes, before the RF signal receiver will accept RF signals from the RF signal transmitter 202. However, as mentioned above, it has been recognised herein that the environment in which a radiotherapy device operates is usually largely free from RF signals, such that any such authentication may be unnecessary. Moreover, even if the devices are configured such that an initial authentication is required when the RF signal transmitter 202 first transmits to the RF signal receiver of a peripheral, it is usually unnecessary for there to be additional or ongoing security requirements for the signals that are subsequently transmitted and received between the RF signal transmitter 202 and the RF signal receiver.

It has been recognised herein that, in addition to being potentially unnecessary, including security or authentication requirements on signals between the RF signal transmitter 202 and a corresponding RF signal receiver may impair the usefulness of those signals. That is; because the RF signal transmitter 202 is generally configured to transmit information regarding pulse timing for the radiotherapy device (although, as detailed below, it may be configured to also or instead transmit other data) to the RF signal receiver, it is generally beneficial for there to be as little delay as possible, between the transmission and the receipt of the signals. It will be appreciated that the distances involved, between a transmitter on a rotating part of a linac and a peripheral on the patient table or elsewhere in the radiotherapy room, are relatively small and as such those distances would not create any discernible delay between transmission and receipt. However, if the RF signal (or, in other examples, another type of wireless signal) between the transmitter and receiver had inherent security embodied therein, that security may cause latency and/or jitter between the transmitted and received signals. As the skilled reader will be aware; 'jitter' is a term used to describe deviation of a signal from its true periodicity. Such latency and/or jitter would potentially degrade the accuracy of any synchronisation between the radiotherapy device and its corresponding peripheral(s). Nonetheless, there may be situations in which it is deemed appropriate to include some security in the signalling, and any potential issues such as latency may be accommodated accordingly.

In operation, the RF signal transmitter 202 is configured to send out an RF signal to the corresponding RF signal receiver on the QA device 208 (and/or to an RF signal receiver in or on another device or entity present in the radiotherapy environment), in order to provide data regarding the pulsed radiation output from the linac 200. That is; the RF signal from the transmitter 202 provides a timing fiducial for any RF receiving circuit close to, or housed in or on, the linac 200. For example, the RF signal transmitter 202 may be configured to send out a signal at each so-called 'trigger point', wherein each trigger point corresponds to a pulse of output radiation from the linac 200 (or to a pulse of RF wave, into the waveguide of the linac 200).

In practice, the RF signal transmitter 202 may be configured to send each signal at a so-called 'pre-trigger time', just before (for example 1 or 2 milliseconds before) the next pulse is about to occur. Sending out a 'pre-trigger' signal of this type can enable the receiving device—which may be a detector or piece of testing equipment—to prepare to function, in order to make its detection or run its test at the correct time for the pulse that is emitted, and not to miss any data.

According to an arrangement, the RF signal transmitter 202 and a corresponding RF signal receiver are configured so that the wireless connection therebetween is kept active at all times, during operation of the linac 200 or during the time period in which the device that comprises the RF signal receiver needs to be coordinated with the linac 200. This is to ensure that the connection does not suffer from excessive connection latency, for example from AGC (Automatic Gain Control) settling and/or negotiation. In such an arrangement, the data emitted by the RF signal transmitter 202 can be pulsed, rather than the RF signal connection itself being pulsed.

According to another arrangement, the wireless signal connection between the RF signal transmitter 202 and a corresponding RF signal receiver can be pulsed, in that the connection can be repeatedly opened and closed.

The RF signal transmitter 202 may be configured for its output signals to have a relatively short propagation distance. For example, the typical range of a 433 MHz unlicensed RF signal transmitter is 30-100 m outdoors or 10-30 m indoors. Again, it has been recognised herein that this feature, which might be regarded as being a disadvantage in some other situations, is acceptable in the present situation because the distance between the RF signal transmitter 202 on the linac 200 and the corresponding RF signal receiver on a peripheral is not going to be significant—particularly when the peripheral is situated or mounted on the patient support surface of the linac, as will often be the case. Moreover, it is potentially desirable in this situation for the RF signal to only as far as the intended receiver, to help bolster security and clarity of the signalling. In practice, a radiotherapy device in the present arrangements is intended to be installed in a concrete 'bunker' (or other enclosed, protected environment) and the RF signal will only be needed to (and be able to) propagate inside that bunker. A typical size for a known radiotherapy 'bunker' is 6×6 m, and they are unlikely to exceed 10 m. Therefore the propagation distance of the RF signal for the RF signal transmitter 202 need not be more than 10 metres, and may indeed be less.

The RF signal transmitter 202 may be configured to transmit other data, as well as or instead of transmitting timing/(pre)trigger data. For example, according to an arrangement, the RF signal transmitter 202 is configured to transmit RF signals that include timing/(pre)trigger data, as detailed above, plus some extra so-called 'meta-data'. The meta-data transmitted may vary according to: which peripheral the linac is to be coordinated with; what function(s) a given peripheral is to carry out, and/or; user requirements or preferences. The capacity of the meta-data is typically limited however it may include information such as, but not limited to: energy; dose-rate and mode of the linac (where this is selectable); field size or confirmation that the field size is set to a standard number (like the 10×10 cm used for calibration); a pulse count number (which may be truncated to a fix bit length modulus); pulse repetition frequency; a unique machine identifier; beam information, and so on. If the linac 200 is capable of providing different output types, the RF signal transmitter may be configured to transmit data regarding its present output type to the corresponding peripheral, which may, in response, configure itself correctly in accordance with that data. This may help cut down on the amount and/or the frequency of manual data entry that is required from the user. In some arrangements, the linac 200 may have one or more standard built in QA beams that have an ID or label, which may form part of the metadata. The linac 200 may also indicate transitory "faults" that might affect measurements. A machine 'beam record' may also be recorded and may be transmitted, in full or in part, within the metadata. The metadata may also comprise 'current machine state' so the peripheral device can identify the start and stop of beams and/or the start and stop of beam segments. The unique identifier may be written into other log files in order to facilitate the merging of data sets for the metadata.

The RF signal transmitter 202 may be configured so as not to transmit a signal corresponding to every pulse of the radiation output from (or every pulse of RF wave input to) the radiotherapy device. It may be configured to transmit a signal at another predetermined interval, or after a predetermined number of pulses of the radiotherapy device, since its last signal was transmitted.

The RF signal transmitter 202 may be configured so as not to transmit all the data that it can transmit, in every signal transmission. For example, some meta data will only need to be sent once, or to be sent at relatively widely-spaced intervals.

Although in the particular arrangement of FIG. 2, the RF signal transmitter 202 is shown as being physically within the beam generation sub-system 204, it will be appreciated that this is not a requirement in all arrangements. The RF (or other wireless) signal transmitter can be physically separate to the beam generating aspects of a radiotherapy device. One or more controllers may be operable to convey data to the RF signal transmitter, for transmission to one or more RF signal receivers.

The RF signal transmitter 202 may be implemented using any suitable mechanical, hardware and/or software components. For example, the RF signal transmitter may be provided as an electronic circuit on a PCB (printed circuit board), located in or on a suitable part of the radiotherapy device. As the skilled reader will appreciate, an RF signal transmitter of the type described herein can be manufactured at relatively low cost and would occupy very little physical space, within a radiotherapy device. Therefore it would be very minimally disruptive to any other aspects of a radiotherapy device, if an RF signal transmitter was included therein.

The RF signal transmitter 202 may be retrofitted to an existing radiotherapy device, or created as a plug-in or add-on for an existing or future radiotherapy device, or incorporated within a future radiotherapy device. It may be permanently attached to or incorporated within the radiotherapy device, or it may be removable therefrom.

The RF signal receiver may be retrofitted to an existing peripheral device, or created as a plug-in or add-on for an existing or future peripheral device, or incorporated within a future peripheral device. It may be permanently attached to or incorporated within the peripheral device, or it may be removable therefrom. According to an arrangement, an RF signal receiver may be provided that includes a 'universal' or common attachment, such as a USB plug, for use with a range of different peripheral devices.

Although the description above in relation to FIG. 2 mentions using an open (ISM) frequency, the RF signal transmitter and receiver may instead be configured to communicate via a 'closed' or secret signal frequency.

The RF signal transmitter, at the radiotherapy device, may also include an RF signal receiver. The RF signal receiver, at the peripheral, may also include an RF signal transmitter. Hence, two-way wireless communication between a radiotherapy device and a peripheral may be achieved. For example, this may enable the radiotherapy device to configure its settings according to the identity or functionality of a given peripheral device, and vice versa.

Although the description above in relation to FIG. 2 mentions using radiofrequency (RF) signalling, other types of wireless signalling may be used instead (or as well). For example, the signalling may be optical, for example Infra-Red (IR). It is possible to use an IR signal that is not particularly directional, in view of the sealed nature of a radiotherapy environment and the lack of signal crowding in its atmosphere, as discussed above. Like RF signals, IR signals tend to have relatively low latency.

It may be possible to use other wireless protocols such as Wifi or Bluetooth™ though they may require enhanced control to accommodate potential latency issues. For example, a Wifi or Bluetooth™ system may require a slightly longer pre-trigger period than an RF system would.

Thus, it has been recognised herein, that the transmission and receipt of a simple, relatively low-security wireless signal, such as but not limited to an RF signal, can help improve the accuracy of the coordination, or synchronisation, of the operations of a radiotherapy device and one or more peripheral systems, sub-systems or devices. Moreover, it has been recognised that the transmission and receipt of a simple, relatively low-security wireless signal in a radiotherapy environment does not give rise to the potential security concerns that are often conventionally associated with such a signal, or at least not to the same extent, because of the largely signal-free atmosphere that exists within a radiotherapy environment. Therefore the potential benefits of this type of signal, such as very low latency and jitter, can be harnessed, for communication between a radiotherapy device and one or more peripheral systems, sub-systems or devices, but still with very low security risks. The potentially short propagation distance of such a signal is also acceptable, as the signal transmitter and receiver(s) are likely to be located close to one another, within a radiotherapy environment.

The use of wireless signals (as opposed to a wired connection) means that any malfunction of a peripheral device should not have any adverse effects on the radiotherapy device. In addition, use of wireless transmitter and receiver devices poses fewer challenges, in terms of physical positioning and location of those devices on the radiotherapy device and peripheral, respectively, as compared to conventional wired set-ups.

The above description mentions the use of a linac (linear accelerator) but other types of radiotherapy device may instead be used.

The term 'peripheral' or 'peripheral' should be understood to include any device, system or sub-system that works in conjunction with, or in communication with, a radiotherapy device, for example the beam generation aspect(s) of a radiotherapy device.

The term 'QA device' should be understood to include, inter alia, any device, system or sub-system that is operable to check or record the correct operation and quality of the radiation output of the radiotherapy device.

Any directional or positional terms used herein such as 'left', 'right', above', 'below', 'upper', 'lower' 'inward', 'outward'. 'longitudinal', lateral' and so on, are used in relative terms and are not intended to be limiting.

Any section headings used herein are merely for organisational purposes. They are not to be construed as limiting or dividing the subject matter disclosed in the application as a whole.

It is to be understood that the above description is intended to be illustrative, and not restrictive. Other implementations will be apparent to those of skill in the art upon reading and understanding the above description. Although the present disclosure has been described with reference to specific example implementations, it will be recognised that the disclosure is not limited to the implementations described, but can be practiced with modification and alteration.

The invention claimed is:

1. A system to deliver radiation to a subject, the system comprising:
   a radiotherapy device configured to provide radiation to a subject via a source of radiation, wherein the source of radiation is configurable to emit a non-continuous beam of radiation, wherein the non-continuous beam of radiation has a first time-related property associated therewith, wherein the radiotherapy device comprises a rotatable member, wherein the radiotherapy device is configurable to operate in conjunction with a peripheral device, and wherein the peripheral device is configured to not rotate with the rotatable member of the radiotherapy device; and
   a wireless signal transmitter, wherein the wireless signal transmitter is configurable to wirelessly transmit a signal comprising data regarding the first time-related property to a wireless signal receiver associated with the peripheral device, wherein the wireless signal transmitter is included on, within, or connected to the rotatable member.

2. The system of claim 1, wherein the wireless signal transmitter is configurable to transmit a radiofrequency (RF) signal.

3. The system of claim 1, wherein the wireless signal transmitter is configured to transmit a wireless signal that comprises non-encrypted data.

4. The system of claim 1, wherein the wireless signal transmitter is configured to wirelessly transmit a second signal to a wireless signal receiver, wherein the second signal comprises data regarding a second property, wherein the second property is associated with at least one of the non-continuous beam of radiation or an aspect of the radiotherapy device.

5. The system of claim 4, wherein the aspect of the radiotherapy device comprises at least one of an identity, an operation, or a configuration of the radiotherapy device.

6. A system to deliver radiation to a subject, the system comprising:
   a radiotherapy device configurable to provide radiation to the subject via a source of radiation, wherein the source of radiation is configurable to emit a non-continuous beam of radiation having a first time-related property, wherein the radiotherapy device comprises a rotatable member;
   a wireless signal receiver configurable to receive a signal comprising data regarding the first time-related property from a wireless signal transmitter, wherein the wireless signal transmitter is provided in, on, within or connected to the rotatable member; and
   a peripheral device configurable to work in conjunction with the radiotherapy device and the wireless signal receiver, wherein the peripheral device is configured to not rotate with the rotatable member of the radiotherapy device.

7. The system of claim 6, further comprising:
   a controller configurable to cause the wireless signal transmitter to wirelessly transmit the signal to the wireless signal receiver.

8. The system of claim 6, wherein the wireless signal transmitter is configurable to wirelessly transmit a second signal comprising data regarding a second property to the wireless signal receiver.

9. The system of claim 8, wherein the second property is associated with the non-continuous beam of radiation.

10. The system of claim 8, wherein the second property is associated with an aspect of the radiotherapy device.

11. A system to deliver radiation to a subject, the system comprising:
    a radiotherapy device configurable to provide radiation to the subject via a source of radiation configurable to emit a non-continuous beam of radiation having a first time related property, wherein the radiotherapy device comprises a rotatable member, wherein the radiotherapy device is configurable to operate in conjunction with a peripheral device, and wherein the peripheral device is configured to not rotate with the rotatable member of the radiotherapy device;
    a wireless signal transmitter included on, within, or connected to the rotatable member;
    a wireless signal receiver associated with the peripheral device; and
    a controller, wherein the controller is configurable to cause the wireless signal transmitter to wirelessly transmit a signal to the wireless signal receiver, and wherein the signal comprises data regarding an aspect of the radiotherapy device.

12. The system of claim 11, wherein the aspect of the radiotherapy device comprises at least one of an identity, an operation, or a configuration of the radiotherapy device.

13. The system of claim 11, wherein the peripheral device comprises an imaging device, a diagnostic device, or a testing device.

14. The system of claim 11, wherein peripheral device is configurable to at least one of check an output of the radiotherapy device, form an image using an output of the radiotherapy device, detect a fault in the operation of the radiotherapy device, or diagnose a fault in the operation of the radiotherapy device.

* * * * *